United States Patent [19]

Fukumoto et al.

[11] Patent Number: 5,495,026
[45] Date of Patent: Feb. 27, 1996

[54] PROCESS FOR PRODUCING CHROMAN

[75] Inventors: Eriko Fukumoto; Masahiro Torihara; Yoshin Tamai, all of Niigata, Japan

[73] Assignee: Kuraray Company Ltd., Kurashiki, Japan

[21] Appl. No.: 305,038

[22] Filed: Sep. 13, 1994

[30] Foreign Application Priority Data

Sep. 28, 1993 [JP] Japan .................. 5-264186

[51] Int. Cl.⁶ .................. C07D 311/58; C07D 311/92
[52] U.S. Cl. .................. 549/389; 549/411; 549/410; 549/408; 549/405; 549/404
[58] Field of Search .................. 549/411, 410, 549/408, 405, 404, 389

[56] References Cited

FOREIGN PATENT DOCUMENTS 60-92283  5/1985  Japan .

*Primary Examiner*—Nicky Chan
*Attorney, Agent, or Firm*—Oblon, Spivak, McClelland, Maier & Neustadt

[57] ABSTRACT

A phenol, a formaldehyde and an unsaturated compound having carbon-carbon double bond are reacted in the presence of a secondary amine and an acid at a temperature of 100° to 250° C., to give a chroman.

8 Claims, No Drawings

PROCESS FOR PRODUCING CHROMAN

BACKGROUND OF THE INVENTION

1. Field of the Invention

The present invention relates to a process for producing chromans.

Chromans are useful as intermediate products for bioactive substances such as tocopherols and pharmaceuticals and for polymeric materials including engineering resins and as stabilizers for organic substances such as fats, oils and synthetic resins.

2. Description of the Related Art

Known processes for producing chromans are as follows.

(1) Ring-closing reaction of an allyl phenol

This process comprises effecting ring closing of an allyl compound obtained by reacting a phenol with an allyl halide, allyl alcohol or a diolefine. See, for example, "DAIYUKIKAGAKU, Vol. 14 Heterocyclic Compounds I, pages 215–217".

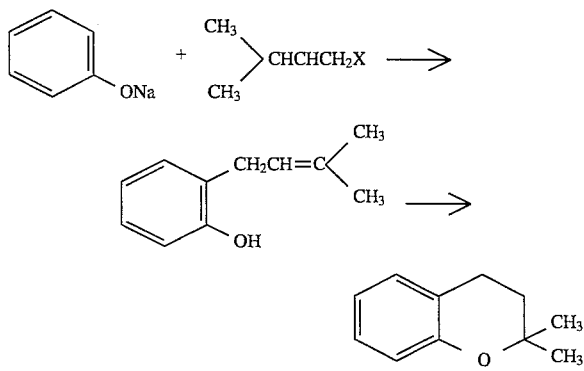

wherein X represents a halogen atom.

(2) Reaction of o-oxybenzyl alcohol with an unsaturated compound.

This process comprises heating a mixture of o-oxybenzyl alcohol and an unsaturated compound with no solvent at a temperature of 180° to 220° C. See, for example, "DAIYUKIKAGAKU, Vol. 14 Heterocyclic Compounds I, page 220".

It is considered that, by this process, there forms an intermediate of the dehydrated product of o-oxybenzyl alcohol, which then undergoes Dieis-Alder reaction with the unsaturated compound. The yield is about 50%.

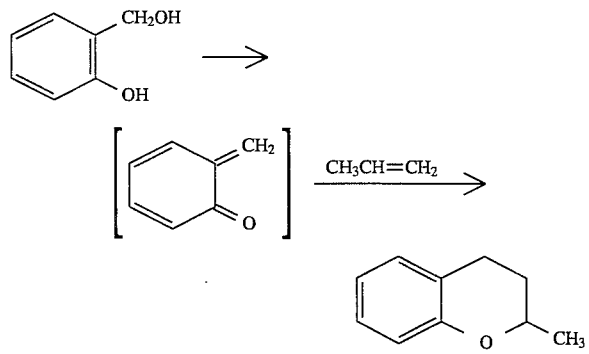

(3) Reaction of the oxidized product of o-[1-(alkylthio)alkyl] phenol with an unsaturated compound The process comprises oxidizing o-[1-(alkylthio)alkyl] phenol with silver oxide under a mild condition, and reacting the oxidized product with a vinyl ether, to obtain a chroman. See, for example, Bull. Chem. Soc. Jpn. , 63 (4) , 1062 (1990).

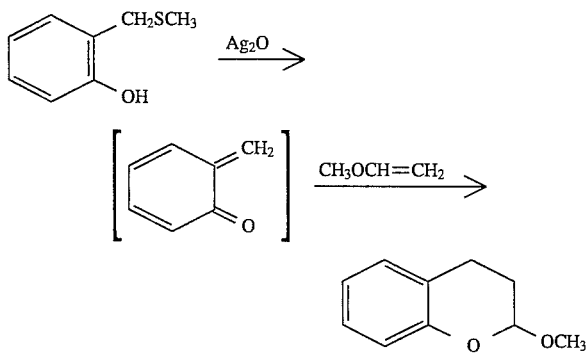

(4) Reaction of a phenol, formaldehyde and unsaturated compound

This process comprises reacting a phenol, formaldedyde and unsaturated compound in a solvent of a hydrocarbon or an aromatic halogenized compound at a temperature of 160° to 250° C., to obtain a chroman. See, for example, Japanese Patent Application Laid-open No. 92283/1985.

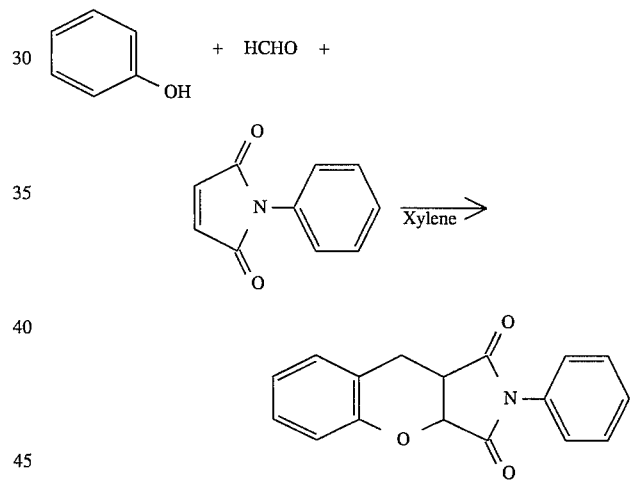

However, the above known processes have the following problems.

That is, the process (1) sometimes cannot produce a chroman depending on the substituent present on the allyl compound or diolefin used and generally leads to a low yield. The process (2), for which it is difficult to produce o-oxybenzyl alcohol in a high yield, is not suitable for commercial production. The reaction of the process (3), which uses a special compound as a starting material and requires an equimolar amount of silver oxide for oxidizing phenol, is also unsuitable for industrial application. The process (4) gives a low yield of 10 to 50%.

SUMMARY OF THE INVENTION

Accordingly, an object of the present invention is to solve the above problems associated with the prior art and to provide chromans in a high yield and by an industrially simple and easy process.

The present inventors have found that reaction of a phenol and an unsaturated compound, both being readily available at a low cost, can give chromans by a one-spot reaction and in a high yield, and completed the invention.

Thus, the present invention provides a process for producing chromans which comprises reacting a phenol, a formaldehyde and an unsaturated compound having carbon-carbon double bond in the presence of a secondary amine and an acid.

DETAILED DESCRIPTION OF THE PREFERRED EMBODIMENTS

The phenol used in the present invention includes those having at least one phenolic hydroxyl group, at least one ortho position of which is not substituted, and its examples are phenol, cresol, naphthol, methoxyphenol, nitrophenol, acetoxytrimethylphenol and trimethylhydroquinone.

Examples of the formaldehyde used in the invention are, besides formaline, linear polymers such as paraformaldedhye and cyclic acetate oligomers such as trioxane and tetraoxane.

In the present invention, as the unsaturated compound having carbon-carbon double bond there can be used any compound having carbon-carbon double bond that is not conjugated with other carbon-carbon double bond except for aromatic compound. Concrete examples are the unsaturated compounds represented by the following formula

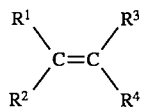

wherein $R^1$ through $R^4$ each represents a hydrogen atom or a linear or branched alkyl group having 1 to 20 carbon atoms which may be substituted, an aryl group, a carbonyl group, a carboxyl group or an ester group.

Examples of the alkyl group which is represented by $R^1$ through $R^4$ are methyl, ethyl, n-propyl, isopropyl, butyl, 2-methylbutyl, t-butyl, n-pentyl, 1-methylpentyl, neopentyl, 4-methylpentyl, hexyl, isohexyl, heptyl, octyl, nonyl, decyl, 4,8,12-trimethyltridecyl, undecyl, dodecyl, tridecil, tetradecyl, pentadecyl, hexadecyl, heptadecyl, octadecyl, nonadecyl and eicosyl. The alkyl group may have substituents such as hydroxyl group and its examples are hydroxymethyl and hydroxyethyl. Examples of the aryl group are phenyl, tolyl, xylyl and naphthyl, and those of ester group are methoxycarbonyl and ethoxycarbonyl.

Concrete examples of the unsaturated compound are hydrocarbon olefins, e.g. 1-octene, 2,6-dimethyl-1-heptene, 2,6,10,14-tetramethyl-1-pentadecene and 2,6-dimethyl-1,5-heptadiene and olefins conjugated with aromatic group, such as styrene. There can also be used unsaturated compounds substituted with an electron donative or electron withdrawing polar group for the double bond, and their examples are acrylic acid esters, e.g. ethyl acrylate, ethyl methacrylate, methyl 3,3-dimethylacrylate, and hydrocarbon alcohols having carbon-carbon double bond, e.g. 2-methyl-2-propen-1-ol, 3-methyl-2-buten-1-ol and 3-methyl-3-buten-1-ol.

The secondary amine used in the invention includes linear secondary amines, e.g. diethylamine and dibutylamine and cyclic secondary amines, e.g. piperidine, pyrrolidine and morpholine.

The acid used in the invention means a saturated aliphatic acid having 2 to 8 carbon atoms, and its examples are acetic acid, propionic acid, butyric acid, 2-methylpropanoic acid, valeric acid, 3-methylbutanoic acid, 2-methylbutanoic acid, hexanoic acid, heptanoic acid and octanoic acid.

In the present invention, it is essential that the reaction of a phenol, a formaldehyde and an unsaturated compound having carbon-carbon double bond be conducted in the presence of a secondary amine and an acid. If the reaction is effected in the presence of a secondary amine only, without an acid, the reaction will stop midway, whereby the desired chroman cannot be obtained. If the reaction is effected in the presence of an acid only, without a secondary amine, the reaction will not proceed at all, whereby the desired chroman cannot be obtained either.

In the present invention, the phenol, formaldehyde and unsaturated compound are used preferably in equimolar amounts, but any of the components may be changed according to its reactivity. On this occasion, based on the amount of the phenol used, other components can be changed within the range of 1 to 20 molar equivalents, preferably with the range of 1 to 5 molar equivalents. The amounts of the secondary amine and acid used can be changed, based on the amount of the phenol, within the range of 0.01 to 5 molar equivalents, in particular within the range of 0.1 to 0.5 molar equivalent.

Although the reaction of the present invention can be effected without solvent, an inert solvent such as toluene or xylene may be used.

The reaction of the present invention can be initiated by mixing the above-mentioned phenol, unsaturated compound having carbon-carbon double bond, formaldehyde, secondary amine and acid and then heating the mixture.

The reaction is effected generally at a temperature of 100° to 250° C.

After completion of the reaction, unreacted matters are removed and then the reaction mixture is purified by crystallization, distillation or like processes, to give an isolated product of the desired chroman.

EXAMPLES

Other features of the invention will become apparent in the course of the following descriptions of exemplary embodiments which are given for illustration of the invention and are not intended to be limiting thereof.

Example 1

[Synthesis of 2,5,7,8-tetramethyl-6-acetoxy-2-hydroxy-methylchroman]

A pressure-proof reaction vessel equipped with a stirrer was charged with 17.5 g (0.09 mole) of 4-acetoxy- 2,3,5-trimethylphenol, 32.5 g (0.45 mole) of 2-methyl-2-propen-1-ol, 3.7 g (0.099 mole) of 80% paraformaldehyde, 1.2 g (0.009 mole) of dibutylamine and 2.7 g (0.045 mole) of acetic acid, and the mixture was reacted, with stirring, at 150° C. for 3 hours.

After completion of the reaction, the excess 2-methyl-2-propen- 1-ol was distilled off, and the residue was recrystallized from n-hexane, to give 23.0 g of the desired product, which was white powder. (Yield: 91.8%)

The obtained compound showed $^1$H-NMR spectrum data as follows.

δ ppm (CDCl$_3$, 300 MHz); 1.24 (3H, m), 1.68–2.15 (2H, m), 2.00 (3H, s), 2.04 (3H, s), 2.10 (3H, s), 2.35 (3H, s), 2.64–2.68 (2H, m) , 3.56–3.68 (2H, m) .

Comparative Example 1

A pressure-proof reaction vessel equipped with a stirrer was charged with 17.5 g (0.09 mole) of 4-acetoxy-2,3,5-trimethylphenol, 32.5 g (0.45 mole) of 2-methyl-2-propen- 1-ol, 3.7 g (0.099 mole) of 80% paraformaldehyde and 2.7 g (0.045 mole) of acetic acid, and the mixture was reacted, with stirring, at 150° C. for 3 hours. However, the desired product 2,5,7,8-tetramethyl-6-acetoxy-2-hydroxy-methylchroman could not be obtained at all.

Comparative Example 2

A pressure-proof reaction vessel equipped with a stirrer was charged with 17.5 g (0.09 mole) of 4-acetoxy-2,3,5-trimethylphenol, 32.5 g (0.45 mole) of 2-methyl-2-propen-1-ol, 3.7 g (0.099 mole) of 80% paraformaldehyde and 1.2 g (0.009 mole) of dibutylamine, and the mixture was reacted, with stirring, at 150° C. for 3 hours. However, the desired product 2,5,7,8-tetramethyl-6-acetoxy-2-hydroxy-methylchroman could not be obtained at all.

Example 2

[Synthesis of 2,5,7,8-tetramethyl-6-acetoxy-2-ethoxycarbonylchroman]

There were mixed 1.9 g (0.01 mole) of 4-acetoxy-2,3,5-trimethylphenol, 9.2 g (0.08 mole) of ethyl methacrylate, 0.3 g (0.011 mole) of paraformaldehyde, 0.13 g (0.001 mole) of dibutylamine and 0.3 g (0.005 mole) of acetic acid, and the mixture was heated under reflux for 15 hours.

After completion of the reaction, the excess methyl methacrylate was distilled off and the residue was recrystallized from n-hexane-ethyl acetate (3:1), to give 2.36 g of the desired product crystal. (Yield: 73.7%)

The obtained compound showed $^1$H-NMR spectrum data as follows.

δ ppm (CDCl$_3$, 300 MHz); 1.19 (3H, t, J= 7.1 Hz), 1.61 (3H, s), 1.82–2.44 (2H, m), 1.95 (3H, s), 2.04 (3H, s), 2.18 (3H, s), 2.33 (3H, s), 2.46–2.69 (2H, m), 4.10–4.17 (2H, q, J= 7.1 Hz).

Example 3

[Synthesis of 2,5,7,8-tetramethyl-6-acetoxy-2-hydroxyethylchroman]

A pressure-proof reaction vessel equipped with a stirrer was charged with 1.9 g (0.01 mole) of 4-acetoxy-2,3,5-trimethylphenol, 8.5 g (0.1 mole) of 3-methyl-3-buten-1-ol, 0.3 g (0.011 mole) of paraformaldehyde, 0.13 g (0.001 mole) of dibutylamine and 0.3 g (0.005 mole) of acetic acid, and the mixture was reacted, with stirring, at 150° C. for 11 hours.

After completion of the reaction, the excess 3-methyl-3-buten-1-ol was distilled off, and the residue was recrystallized from n-hexane-diethyl ether (2:1), to give 1.86 g of the desired product, which was white powder. (Yield: 63.6%)

The obtained compound showed $^1$H-NMR spectrum data as follows.

δ ppm (CDCl$_3$, 300 MHz); 1.30 (3H, m), 1.72–1.82 (2H, m), 1.88–1.98 (2H, m), 2.00 (3H, s), 2.04 (3H, s), 2.09 (3H, s), 2.34 (3H, s), 2.39 (1 H, br. s), 2.63–2.68 (2H, m), 3.82–3.98 (2H, m).

Example 4

[Synthesis of 2,8-dimethyl-2-hydroxymethylchroman]

A pressure-proof reaction vessel equipped with a stirrer was charged with 16.2 g (0.15 mole) of o-cresol, 54.1 g (0.75 mole) of 2-methyl-2-propen-1-ol, 6.2 g (0.165 mole) of 80% paraformaldehyde, 1.9 g (0.015 mole) of dibutylamine and 4.5 g (0.075 mole) of acetic acid, and the mixture was reacted, with stirring, at 170° C. for 6 hours.

After completion of the reaction, the excess 2-methyl-2-propen-1-ol was distilled off, and the residue was purified by silica gel chromatography (eluent: n-hexane-ethyl acetate (4:1)), to give 26.0 g of the desired product, which was oily liquid (Yield: 78.0%)

The obtained compound showed $^1$H-NMR spectrum data as follows.

δ ppm (CDCl$_3$, 300 MHz); 1.29 (3H, m), 1.69–2.09 (2H, m), 2.20 (3H, s), 2.73–2.93 (2H, m), 3.62 and 3.69 (2H, AB-type, J= 11.8 Hz), 6.75–6.80 (1 H, m), 6.93–7.00 (2H, m).

Example 5

[Synthesis of vitamin E acetate (tocopherol acetate)]

A pressure-proof reaction vessel equipped with a stirrer was charged with 7.0 g (0.036 mole) of 4-acetoxy- 2,3,5-trimethylphenol, 50.0 g (0.18 mole) of 2,6,10,14-tetramethyl-1-pentadecene, 1.4 g (0.045 mole) of 80% paraformaldehyde, 0.5 g (0.0036 mole) of dibutylamine and 1.1 g (0.018 mole) of acetic acid, and the mixture was reacted, with stirring, at 170° C. for 4 hours.

After completion of the reaction, undissolved matter was removed by filtration, and n-hexane was then added to the filtrate. The mixture was washed successively with 5% aqueous sulfuric acid, saturated aqueous sodium bicarbonate and saturated brine in this order and then the solvent was distilled off. The residue was purified by silica gel chromatography (eluent: n-hexane-ethyl acetate (20:1)), to give 13.1 g of the desired product, which was oily liquid (Yield: 75.0%)

The obtained compound showed $^1$H-NMR spectrum data as follows.

δ ppm (CDCl$_3$, 300 MHz); 0.85–0.90 (12H, m), 1.04–1.20 (6H, m), 1.25 (3H, s), 1.22–1.48 (12H, m), 1.49–1.64 (3H, m), 1.71–1.88 (2H, m), 2.00 (3H, s), 2.04 (3H, s), 2.11 (3H, s), 2.34 (3H, s), 2.58–2.64 (2H, m).

Obviously, numerous modification and variations of the present invention are possible in light of the above teachings. It is therefore to be understood that within the scope of the appended claims, the invention may be practiced otherwise than as specifically described herein.

What is claimed is:

1. A process for producing chromans which comprises reacting a phenol, a formaldehyde and an unsaturated compound having carbon-carbon double bond in the presence of a secondary amine and an acid, wherein said phenol is a compound having at least one phenolic hydroxyl group, at least one ortho position which is not substituted, and said unsaturated compound is a compound having a carbon-carbon double bond that is not conjugated with another carbon-carbon double bond except in an aromatic moiety.

2. The process according to claim 1, wherein said formaldehyde is used in an amount of 1 to 20 molar equivalents based on the amount of said phenol.

3. The process according to claim 1, wherein said unsaturated compound having carbon-carbon double bond is used in an amount of 1 to 20 molar equivalents based on the amount of said phenol.

4. The process according to claim 1, wherein said secondary amine is used in an amount of 0.01 to 5 molar equivalents based on the amount of said phenol.

5. The process according to claim 1, wherein said acid is used in an amount of 0.01 to 5 molar equivalents based on the amount of said phenol.

6. The process according to claim 1, wherein said reaction is conducted at a temperature of 100° to 250° C.

7. The process according to claim 1, wherein said unsaturated compound having at least one carbon-carbon double bond is a compound represented by the following formula

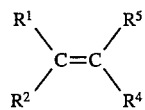

wherein $R^1$ through $R^4$ each represents a hydrogen atom or a linear or branched alkyl group having 1 to 20 carbon atoms which may be substituted, an aryl group, a carbonyl group, a carboxyl group or an ester group.

8. The process according to claim 1, wherein said phenol is a compound selected from the group consisting of phenol, cresol, naphthol, methoxyphenol, nitrophenol, acetoxytrimethylphenol and trimethylhydroquinone.

* * * * *